(12) United States Patent
Naddaff et al.

(10) Patent No.: US 11,229,768 B2
(45) Date of Patent: Jan. 25, 2022

(54) WEARABLE RESPIRATION MANAGEMENT DEVICE

(71) Applicant: Bose Corporation, Framingham, MA (US)

(72) Inventors: Paul Rene Naseeb Naddaff, Newton, MA (US); Kemal Kulovic, Arlington, MA (US); John Andrew Trotter, Sudbury, MA (US)

(73) Assignee: Bose Corporation, Framingham, MA (US)

( * ) Notice: Subject to any disclaimer, the term of this patent is extended or adjusted under 35 U.S.C. 154(b) by 265 days.

(21) Appl. No.: 16/414,048

(22) Filed: May 16, 2019

(65) Prior Publication Data
US 2020/0360651 A1 Nov. 19, 2020

(51) Int. Cl.
*A61M 21/02* (2006.01)
*A61B 5/08* (2006.01)
(Continued)

(52) U.S. Cl.
CPC .......... *A61M 21/02* (2013.01); *A61B 5/0816* (2013.01); *A61B 5/486* (2013.01); *A61B 5/4809* (2013.01);
(Continued)

(58) Field of Classification Search
CPC ............. A61M 21/00–02; A61B 5/681; A61B 5/6824; A61B 5/486
See application file for complete search history.

(56) References Cited

U.S. PATENT DOCUMENTS

| 10,046,234 B2 | 8/2018 | Perdigon Rodriguez et al. |
| 10,048,703 B1 | 8/2018 | Shaker et al. |

(Continued)

FOREIGN PATENT DOCUMENTS

| CN | 104665800 A | 6/2015 |
| EP | 1902701 A2 | 3/2008 |

(Continued)

OTHER PUBLICATIONS

Basslet by Lofelt, describing a wearable subwoofer, accessed at https://lofelt.com/the-basslet on May 10, 2019.
(Continued)

*Primary Examiner* — Thaddeus B Cox
(74) *Attorney, Agent, or Firm* — Hoffman Warnick LLC (57) ABSTRACT

Various implementations include wearable devices and methods for managing respiration and user health. In some particular implementations, a wearable device includes: a mount sized to couple with a body part of a user; and a housing coupled with the mount. The housing at least partially contains: a contact element for applying pressure to the body part; and an actuator coupled with the contact element, the actuator configured to actuate the contact element in applying pressure to the body part according to a prescribed pattern. The prescribed pattern includes at least two repetitions, each repetition having: a first segment at a progressively increasing pressure; a second segment at a substantially constant pressure, following the first segment; a third segment at a progressively decreasing pressure, following the second segment; and a fourth segment at a substantially constant pressure that is less than the substantially constant pressure of the second segment.

17 Claims, 7 Drawing Sheets

(51) Int. Cl.
  *A61B 5/00* (2006.01)
  *A61B 7/00* (2006.01)
  *A61M 21/00* (2006.01)
(52) U.S. Cl.
  CPC ............. *A61B 5/681* (2013.01); *A61B 5/6824* (2013.01); *A61B 5/7405* (2013.01); *A61B 7/003* (2013.01); *A61B 2560/0242* (2013.01); *A61M 2021/0027* (2013.01); *A61M 2021/0088* (2013.01); *A61M 2230/42* (2013.01)

(56) References Cited

U.S. PATENT DOCUMENTS

| | | | | |
|---|---|---|---|---|
| 2008/0071202 | A1* | 3/2008 | Nardi | A61B 5/6829 601/98 |
| 2012/0065561 | A1 | 3/2012 | Ballas et al. | |
| 2013/0190554 | A1* | 7/2013 | Vogt | A61M 21/00 600/27 |
| 2015/0073313 | A1* | 3/2015 | Sunnen | A61M 21/02 601/15 |
| 2015/0101788 | A1 | 4/2015 | Smith et al. | |
| 2016/0058376 | A1* | 3/2016 | Baek | A61B 5/7278 340/870.07 |
| 2016/0255944 | A1 | 9/2016 | Baranski et al. | |
| 2016/0346501 | A1* | 12/2016 | Hooper | A61B 5/4836 |
| 2019/0030278 | A1 | 1/2019 | Kremer et al. | |
| 2019/0099290 | A1 | 4/2019 | Thomas et al. | |
| 2019/0110950 | A1 | 4/2019 | Smith et al. | |
| 2020/0178887 | A1* | 6/2020 | Correa Ramirez | A61B 5/4806 |

FOREIGN PATENT DOCUMENTS

| | | |
|---|---|---|
| JP | 2005133553 A | 5/2005 |
| WO | 2015145471 A1 | 10/2015 |
| WO | 2018169484 A1 | 9/2018 |

OTHER PUBLICATIONS

PCT International Search Report and Written Opinion for International Application No. PCT/US2020/029147, dated Sep. 14, 2020, 18 pages.

* cited by examiner

WEARABLE RESPIRATION MANAGEMENT DEVICE

TECHNICAL FIELD

This disclosure generally relates to devices and approaches for managing user health by way of respiration. More particularly, the disclosure relates to wearable devices and related control approaches for managing user respiration.

BACKGROUND

Respiration management can be used to manage various wellness parameters. For example, some respiration management approaches aim to reduce stress, increase awareness and/or control blood pressure. Some respiration management approaches rely upon audible cues to trigger breathing, in terms of frequency, depth of breath, length of breath, etc. However, audible cues can be impractical for effective respiration management in many circumstances, such as in a professional setting or while sleeping.

Other respiration management approaches rely upon haptic cues to trigger breathing. One particular approach relies upon a wearable device that vibrates to provide a respiration management cue. However, with the proliferation of electronic devices that use vibration-based notifications, a vibrational respiration management cue can prove confusing to users. Additionally, vibrational respiration management cues can trigger a stress response in users who associate such haptic cues with reminders or notifications (e.g., e-mail reminders, text notifications and/or incoming call notifications).

SUMMARY

All examples and features mentioned below can be combined in any technically possible way.

Various implementations include devices for managing user respiration. In other implementations, methods for managing user respiration are disclosed.

In some particular aspects, a wearable device for managing respiration and health of a user is disclosed. The device can include: a mount sized to couple with a body part of the user; and a housing coupled with the mount, the housing at least partially containing: a contact element for applying pressure to the body part of the user; and an actuator coupled with the contact element, the actuator configured to actuate the contact element in applying pressure to the body part of the user according to a prescribed pattern, the prescribed pattern including at least two repetitions, each repetition having: a first segment at a progressively increasing pressure; a second segment at a substantially constant pressure, following the first segment; a third segment at a progressively decreasing pressure, following the second segment; and a fourth segment at a substantially constant pressure that is less than the substantially constant pressure of the second segment.

In other particular aspects, a computer-implemented method of managing respiration and health of a user with a wearable device is disclosed. The method can include: actuating a contact element to apply pressure to a body part of the user according to a prescribed pattern, the prescribed pattern including at least two repetitions, each repetition having: a first segment at a progressively increasing pressure; a second segment at a substantially constant pressure, following the first segment; a third segment at a progressively decreasing pressure, following the second segment; and a fourth segment at a substantially constant pressure that is less than the substantially constant pressure of the second segment.

In additional particular aspects, a wearable device for managing respiration and health of a user is disclosed. The device can include: a mount sized to couple with a body part of the user; and a housing coupled with the mount, the housing at least partially containing: a heat transfer element configured to at least one of heat or cool the body part of the user; and a controller coupled with the heat transfer element, the controller configured to actuate the heat transfer element in the at least one of heating or cooling the body part of the user according to a prescribed pattern, the prescribed pattern including at least two repetitions, each repetition having: a first segment at a progressively increasing or decreasing temperature; a second segment at a substantially constant temperature, following the first segment; a third segment at a progressively decreasing or increasing temperature, following the second segment; and a fourth segment at a substantially constant temperature that is distinct from the substantially constant temperature of the second segment.

In additional particular aspects, a wearable device for managing respiration and health of a user is disclosed. The device can include: a mount sized to couple with a body part of the user; and a housing coupled with the mount, the housing at least partially containing: a transducer configured to transmit an acoustic output into the body part of the user; and a controller coupled with the transducer, the controller configured to actuate the transducer to provide an audio output according to a prescribed pattern, the prescribed pattern including at least two repetitions, each repetition having: a first segment at a progressively increasing or decreasing audio modality level; a second segment at a substantially constant audio modality level, that follows the first segment; a third segment at a progressively decreasing or increasing audio modality level, that follows the second segment; and a fourth segment at a substantially constant audio modality level that is distinct from the substantially constant audio modality level of the second segment.

Implementations may include one of the following features, or any combination thereof.

In particular cases, the mount is sized to fit on a wrist of the user, an arm of the user, an ankle of the user, a leg of the user, a waist of the user or a portion of a head of the user.

In certain aspects, the substantially constant pressure at the second segment is a maximum applied pressure for the prescribed pattern, and is applied for a period of at least approximately 0.1 second to approximately five seconds, and the third segment at the progressively decreasing pressure is applied for a period of approximately four seconds to approximately 20 seconds, where managing respiration in the user includes at least one of guided breathing or breathing entrainment.

In some implementations, the at least two repetitions are separated in time by less than one second.

In certain cases, a later one of the repetitions immediately follows a preceding one of the repetitions.

In particular aspects, the at least two repetitions include at least five to nine repetitions.

In some implementations, the at least two repetitions include up to 500 repetitions.

In certain cases, the housing further includes a controller for controlling the actuator.

In some aspects, the wearable device further includes a biometric monitoring system coupled with the controller, where the controller is configured to adjust the prescribed pattern according to at least one detected biometric condition indicator detected by the biometric monitoring system deviating from a corresponding threshold.

In certain implementations, the controller is configured to receive commands from a smart device proximate the wearable device.

In particular cases, the controller is configured to initiate the prescribed pattern based upon at least one of: (a) a periodic schedule for the user, (b) a biometric indicator indicating an elevated stress level for the user, or (c) actuation by the user.

In certain aspects, the actuator includes an electro-mechanical actuator, a pneumatic actuator or a flexible fiber actuator.

In some implementations, the contact element includes an arcuate contact surface for at least partially wrapping around the body part of the user while applying pressure to the body part of the user, or a substantially planar contact surface for applying pressure to the body part of the user.

In particular aspects, the wearable device further includes a heat transfer member configured to at least one of heat or cool the body part of the user.

In certain cases, the computer-implemented method further includes: monitoring at least one biometric condition of the user; and adjusting the prescribed pattern according to the at least one biometric condition deviating from a corresponding threshold.

In some implementations, the wearable device including the heat transfer element further includes: a contact element for applying pressure to the body part of the user; and an actuator coupled with the contact element, the actuator configured to actuate the contact element in applying pressure to the body part of the user.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

This disclosure is based, at least in part, on the realization that a pressure-based, temperature-based and/or acoustic-based respiration management approach can be beneficially incorporated into a wearable device to improve user health. For example, a wearable device can include a contact element and an actuator for applying pressure to a user's body and/or heating/cooling the user's body according to a prescribed pattern in order to manage that user's respiration, and by extension, that user's health. In other examples, a wearable device can include a transducer for transmitting soundwaves into a user's body part according to a prescribed pattern in order to manage that user's respiration, and by extension, that user's health.

Commonly labeled components in the FIGURES are considered to be substantially equivalent components for the purposes of illustration, and redundant discussion of those components is omitted for clarity.

As used herein, the term "guided breathing" is a respiration management technique involving consciously recognizable cues. In the various implementations described herein, these consciously recognizable cues can include applying pressure at a particular level and/or in a particular pattern, such that the user is highly likely to be conscious of the cue. An analogy in terms of audible respiration management cues could include audio playback of a phrase such as, "Breath in now", or "Take a deep breath". When the user hears the cue, she may consciously choose to take a deep breath following the cue.

In contrast to guided breathing, "breathing entrainment" is a respiration management technique involving subconscious cues. In the various implementations described herein, these subconscious cues can include applying pressure at a particular level and/or in a particular pattern, such that the user is less likely to be conscious of the cue. An analogy in terms of audible respiration management cues could include subtle changes in a continuous audio playback file or stream, such that the user does not recognize the change. In a particular example, a user may be listening to a song, or a background sound (e.g., ocean waves crashing), and a breathing entrainment-type cue can include an audio adjustment to the playback, e.g., adjusting the volume of the playback, adjusting a tone setting of the playback in marginal way so as to avoid conscious detection by the user, or panning audio playback between left and right channels. It is understood that the various implementations described herein can be useful in both guided breathing and breathing entrainment.

As noted herein, some conventional respiration management approaches rely upon haptic cues to trigger breathing. Particular approaches rely upon a wearable device (e.g., a watch or other wrist-worn device) that vibrates to provide a respiration management cue. However, these conventional vibration-based notifications can be ineffective at managing respiration. In particular, in many modern societies, conventional vibration-based notifications have developed an association with stress-inducing events, such as reminders or notifications (e.g., e-mail reminders, text notifications and/or incoming call notifications). Respiration management is often used to reduce user stress, or at least prevent an increase in the user's stress level. As such, these conventional vibration-based respiration management cues can have little or no benefit to a user when attempting to manage respiration. Additionally, these conventional vibration-based respiration management cues can be ineffective in breathing entrainment, because these conventional vibration-based cues are so engrained in many users as stress-inducing that they cannot remain subconscious.

In contrast to conventional respiration management approaches, various implementations include devices and approaches for managing respiration (and by extension, health) using pressure-based and/or temperature-based haptic cues. In particular cases, the devices and approaches are configured to apply pressure to the body part of a user and/or heating/cooling the user's body part according to a prescribed, multi-segmented pattern. The application of pressure and/or temperature change according to this pattern can be used for guided breathing and/or breathing entrainment.

Figure 1:
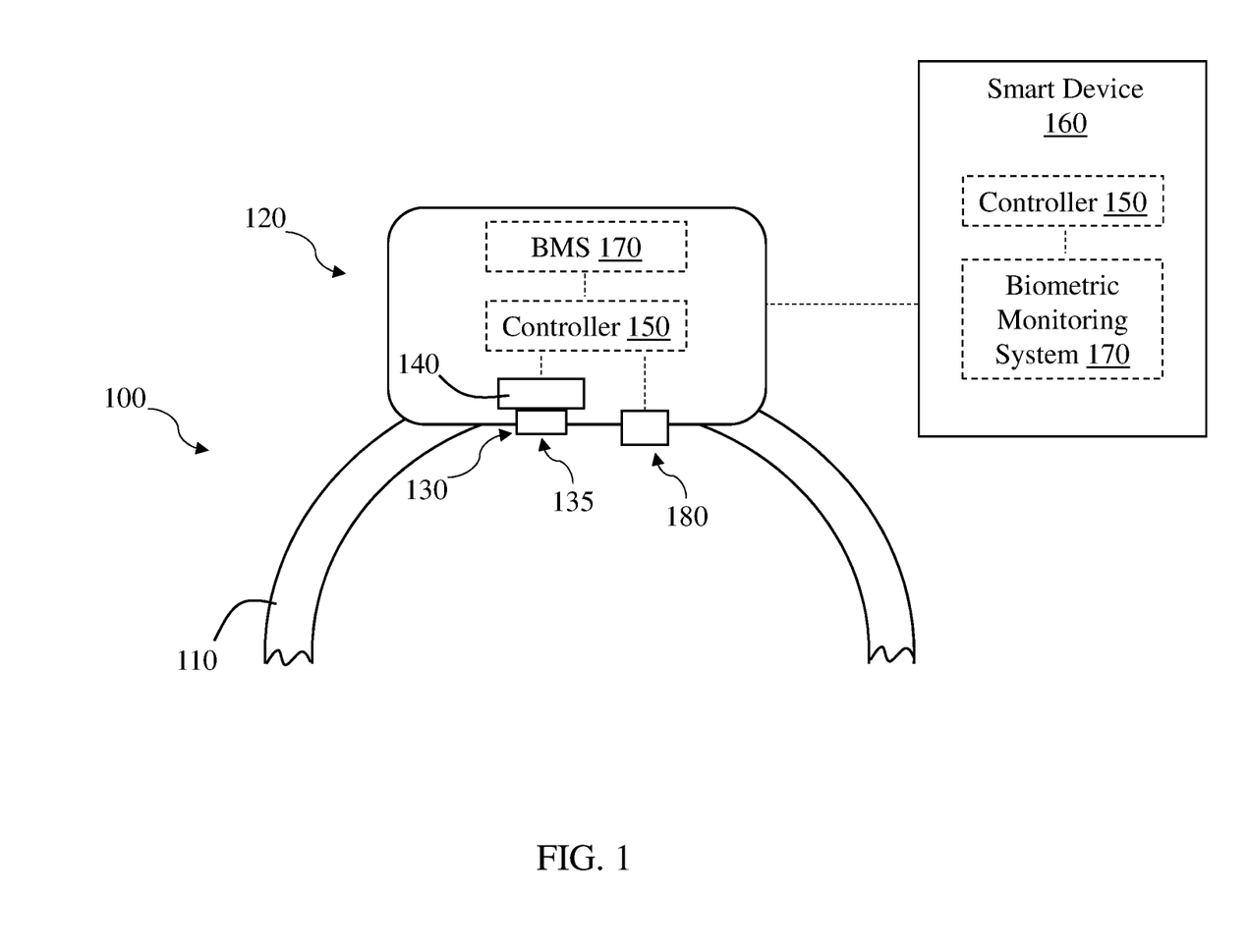
FIG. 1 is a schematic depiction of a wearable device and data flows within that device and between that device and a smart device, according to various disclosed implementations.

FIG. 1 is a schematic depiction of a wearable device 100 for managing user respiration. In various implementations, the wearable device 100 includes a mount 110 that is sized to couple with a body part of a user (mount 110 shown in partial cutaway view). In particular cases, the mount 110 is sized to fit on or around the wrist of a user, e.g., as a bracelet or watch. However, in other cases, the mount 110 is sized to couple with various user body parts, e.g., on or around the arm or leg, on or around the ankle, around the waist, on a portion of the head (e.g., on or in the ear or around the neck) resting over the shoulder(s), on or around one or more fingers or toes, etc. That is, the mount 110 can take any form factor capable of coupling with a body part of the user.

In additional implementations, the mount 110 is part of a wearable audio device, such as a set of eye glasses (e.g., audio glasses), headphones, earphones or earbuds, wearable speakers, wrist-worn speakers, etc. In these cases, the mount 110 can be integral with any mounting structure in that wearable audio device, such as the arm(s) of the glasses, or the earcup of the headphones.

Coupled with the mount 110 is a housing 120, which can include a separate physical housing, or an extension of the material that forms the mount 110. That is, the housing 120 can include a separate compartment for holding one or more components, or can be formed as an integral portion of the mount 110. In any case, the housing 120 at least partially contains a contact element 130 for applying pressure to the body part of the user, and an actuator 140 that is coupled with the contact element 130.

In particular cases, the contact element 130 includes a contact surface for contacting the body part of the user. In some cases, the contact element 130 can include a pad or other cushioned material (e.g., silicone) suitable for repeated contact with the user's skin. The contact element 130 can be mechanically coupled with the actuator 140, and in some cases, acts as an extension of the actuator 140.

As described herein, in various implementations, the actuator 140 can include an electro-mechanical actuator, a pneumatic actuator or a flexible fiber actuator. Specific examples of actuators 140 are described according to the various implementations herein. For example, an electro-mechanical actuator can include a circuit configured to control movement of a mechanical contact element 130 in response to an electrical signal. A pneumatic actuator can be configured to control movement of a contact element 130 using a pneumatic fluid. A flexible fiber actuator can include one or more fibers that are configured to expand and contract in response to an actuation command (e.g., electrical signal or mechanical motion). In these cases, the contact element 130 can include a surface or covering over the flexible fiber.

In various implementations, the actuator 140 is configured to move according to instructions received from one or more local or remote controllers.

As shown in FIG. 1 in phantom, in various implementations, the wearable device 100 includes a controller 150 coupled with the actuator 140, for controlling its movement. In various implementations, the controller 150 controls movement of the actuator 140 in response to a command, e.g., made locally at the wearable device 100, or via a connected smart device (e.g., a smart phone, tablet, smart speaker or smart appliance) 160. In some cases, the controller 150 controls movement of the actuator 140 according to a prescribed pattern. In certain cases, the controller 150 can include a communications module for communicating with one or more other devices, e.g., a connected smart device. The controller 150 can include a processor and logic for controlling movement of the actuator 140 according to the prescribed pattern. The controller 150 and actuator 140 can be physically connected, e.g., via a hard-wired connection, or in other cases, the controller 150 and actuator are wirelessly coupled via any connection described herein (e.g., BLE, WiFi, Zigbee, etc.). While the controller 150 is shown located at the wearable device 100 (e.g., in housing 120), it is understood that the controller 150 can be located in a separate device, e.g., a connected smart device. In these cases, the controller 150 can communicate with the actuator 140 via conventional hard-wired and/or wireless means to control movement of the actuator 140, and ultimately, application of pressure to the user (and/or heating/cooling as described herein).

The controller 150 may be implemented as a chipset of chips that include separate and multiple analog and digital processors. The controller 150 may provide, for example, for coordination of other components of the wearable device 100, such as control of user interfaces (not shown) and applications run by the controller 150. The memory in controller 150 can include, for example, flash memory and/or non-volatile random access memory (NVRAM). In some implementations, instructions (e.g., software) are stored in an information carrier. The instructions, when executed by one or more processing devices (e.g., the processor or microcontroller in controller 150), perform one or more processes, such as those described elsewhere herein. The instructions can also be stored by one or more storage devices, such as one or more (e.g. non-transitory) computer- or machine-readable mediums (for example, the memory, or memory on the processor/microcontroller). As described herein, the controller 150 (e.g., memory, or memory on the processor/microcontroller) can include a control system including instructions for controlling respiration management functions according to various particular implementations. It is understood that portions of the controller 150 (e.g., instructions) could also be stored in a remote location or in a distributed location, and could be fetched or otherwise obtained by the controller 150 (e.g., via any communications protocol described herein) for execution.

In some implementations, the wearable device 100 also includes a biometric monitoring system (BMS) 170 coupled with the controller 150 for detecting one or more biometric condition indicators about the user. The biometric monitoring system 170 can be located at the wearable device 100, however, in other cases, at least a portion of the biometric monitoring system 170 can be located at a distinct device, e.g., smart device 160 or another wearable device (e.g., a smart watch, pedometer, etc.).

In still further implementations, the wearable device 100 includes a heat transfer member 180 connected with the controller 150 that is configured to heat and/or cool the body part of the user. The heat transfer member 180 can include a fluid-based heating/cooling device (e.g., including a heat exchanger and a fluid conduit, an electrical heating/cooling device (e.g., a resistor), or a Peltier effect device) The heat transfer member 180 can include a controller and/or regulator for limiting heating/cooling, and for responding to commands from the controller 150.

The wearable device 100 can also include a sensor system (not shown), which can include one or more movement sensors, such as accelerometers gyroscopes and/or magnetometers. In some particular implementations, the sensor system can include a single IMU having three-dimensional (3D) accelerometers, gyroscopes and a magnetometer. The sensor system on the wearable device 100 can also include one or more interface(s) for receiving commands at the wearable device 100. For example, the sensor system can include an interface permitting a user to initiate functions of the wearable device 100. In other implementations one or more portions of the sensor system can be located at another device capable of indicating movement of the user, inertial information about the user or other information useful in managing respiration of the user. For example, in some cases, the sensor system can include an IMU physically housed in a hand-held device such as a pointer, or in another wearable device (e.g., wearable audio device). In particular example implementations, at least one of the sensors can be housed in a wearable electronic device distinct from the wearable device 100, such as where the wearable device 100 includes headphones and an IMU is located in a pair of glasses, a watch or other wearable electronic device.

As described herein, the actuator 140 is configured to actuate (i.e., translate or otherwise move) the contact element 130 in applying pressure to the body part of the user according to a prescribed pattern. Examples of guided respiration and/or respiration entrainment patterns that can be implemented with the wearable device 100 are described in U.S. patent application Ser. No. 16/045,980 (US Publication No. 2019/0030278, "Entraining Respiration", filed on Jul. 26, 2018), which is incorporated herein by reference in its entirety.

In various particular implementations, the prescribed pattern executed by the wearable device 100 includes at least two repetitions. In certain implementations, each of the repetitions includes: a) a first segment at a progressively increasing pressure; b) a second segment that follows the first segment, at a substantially constant pressure; c) a third segment that follows the second segment, at a progressively decreasing pressure; and d) a fourth segment that follows the third segment, at a substantially constant pressure. The fourth segment, which is of substantially constant pressure, is executed at a pressure that is less than the substantially constant pressure of the second segment. As described herein, the term "substantially constant" can refer to a value that remains the same throughout the entire segment, within a small range of variation (e.g., less than approximately 1% variation).

In the first segment, the actuator 140 translates or otherwise moves (e.g., protrudes or constricts) the contact element 130 in contact with the user (if not already contacting the user's body) and increases the pressure against the user's body part. The first segment can last for a period of several seconds or more, e.g., approximately four seconds to approximately 20 seconds.

In the second segment, the actuator 140 holds the contact element at a substantially constant pressure, which is approximately equal to the peak pressure applied during the second segment (e.g., within 1-3% variation). This substantially constant pressure in the second segment is a maximum applied pressure for the entire prescribed pattern, and in some cases, is applied for a period of at least approximately 0.1 second to approximately five seconds.

In the third segment, the actuator 140 translates or otherwise moves (e.g., retracts or expands) the contact element 130 to apply less pressure to the body part of the user. In some cases, the third segment is applied at the progressively decreasing pressure for a period of approximately four seconds to approximately 20 seconds. In some cases, the third segment lasts for a period that is substantially equal to the period of the first segment. However, in other cases, the first segment and the third segment have different periods.

In the fourth segment, the actuator 140 maintains the contact element 130 at a substantially constant pressure equal to or less than approximately the lowest pressure in the third segment, and less than the constant pressure of the second segment. This substantially constant pressure can be maintained for approximately 0.1 seconds to approximately 10 seconds. The pressure applied in the fourth segment can be equal to the starting, or baseline pressure applied to the user's body in the first segment, and in some cases, is equal to zero or a nominal pressure measurement. That is, in various implementations, the fourth segment is a zero-pressure or nominal-pressure segment.

In particular cases, the second segment and the fourth segment can be punctuated with a brief (e.g., less than one second) increase or decrease in pressure to provide a signal to the user that the hold is over. For example, in the case of the second segment, at approximately the end of that segment (e.g., within seconds prior to the segment concluding), the pressure can be increased or decreased to signal the user that the pressure hold associated with that segment is over. In some cases, a pressure increase is used to trigger the user of the impending conclusion of each of the second segment and the fourth segment (e.g., where the second segment is followed by a pressure drop in the third segment, and the fourth segment is an approximately zero or nominal pressure segment).

In some cases, as noted herein, the fourth segment in a first or non-final repetition is immediately (or nearly immediately, such as within fractions of a second) followed by the first segment in the succeeding repetition. However, in other cases, the first segment in the succeeding repetition follows the fourth segment in the preceding repetition after a delay (e.g., of five or more seconds). In cases where the fourth segment in a succeeding repetition immediately (or nearly immediately) follows the first segment in the preceding repetition, the first segment may progressively increase the pressure from the substantially constant pressure level established by the fourth segment.

In some example implementations, the four segments in a given repetition can be described according to pressure levels, in relative terms. For example: First segment: pressure level zero (0) progressing to pressure level five (5); Second Segment: maintaining pressure level five (5) for a period; Third Segment: pressure level five (5) decreasing to pressure level one (1) or zero (0); Fourth Segment: pressure level one (1) or zero (0) maintained for a period. In these cases, the First Segment in the next repetition can immediately follow the Fourth Segment in the prior repetition.

In some cases, the pattern includes several repetitions or more. In particular examples, the pattern includes five to nine repetitions. In additional examples, the user can define the number of repetitions, which in some cases can include between one repetition (e.g., for brief stress control) and 500 repetitions (e.g., for an extended guided breathing exercise). In various implementations, repetitions are not separated in time. That is, at the end of the fourth segment of a repetition, the first segment of the following repetition will begin approximately immediately (e.g., within a second or two). In other cases, the repetitions are separated by several seconds, such that the end of the fourth segment of a repetition is separated from the beginning of the first segment of the following repetition by at least five seconds.

In various implementations, as noted herein, managing respiration in the user includes guided breathing and/or breathing entrainment. In either case, the prescribed pattern can have a similar relationship, in terms of the length of segments and succession of segments. However, in the case of guided breathing, the pressure applied at each segment can be greater than the pressure applied in the case of breathing entrainment. Pressure ranges described herein can be used for guided breathing, and in some cases, the lower end of those pressure ranges can be used for breathing entrainment. In various implementations, the maximum pressure applied by the wearable devices will not exceed that of conventional blood-pressure monitors, e.g., approximately 250 mm Hg.

As also described herein, this multi-segment, repeated pattern (with extended periods), has a distinct (and more significant) impact in respiration management than a vibrational pattern that merely oscillates between two modes. That is, applying pressure to the user's body according to the prescribed pattern can effectively guide breathing, and in some cases, entrain breathing for users while maintaining or reducing stress levels. In some cases, the wearable device 100 can apply pressure according to this pattern on a periodic or continuous basis to guide breathing and/or entrain respiration. In particular cases, the wearable device 100 can be configured to apply pressure to the user's body according to the prescribed pattern while the user is active, resting (awake), and/or asleep.

Figure 2:
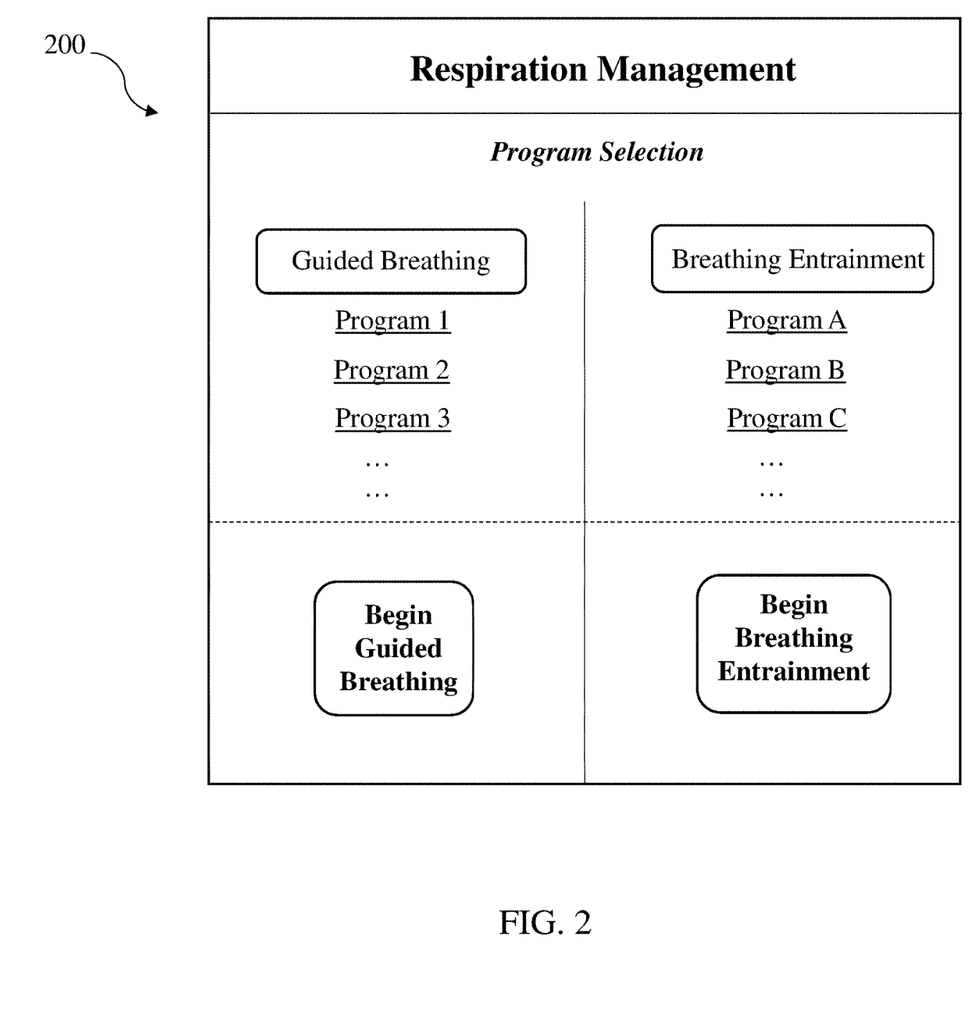
FIG. 2 shows an example interface for a respiration management application according to various implementations.

In certain implementations, the controller 150 is configured to initiate the prescribed pattern based upon one or more of: a periodic schedule for the user; a biometric indicator that indicates an elevated stress level for the user, or actuation by the user. For example, the controller 150 can be configured to initiate the prescribed pattern in a program aimed to guide user breathing or entrain that user's breathing. In some cases, as shown in FIG. 2, the controller 150 can include or otherwise communicate with an interface 200, such as an interface located on the housing 120 and/or a connected smart device (e.g., smart device 160, FIG. 1). In various implementations, the interface 200 is rendered via an application (e.g., software application) that is downloaded or otherwise accessible at the wearable device 100 or the connected smart device 160, or is accessible using one or more cloud-based networks. The interface 200 allows the user to choose between one or more guided breathing programs (Guided Breathing) or breathing entrainment programs (Breathing Entrainment). These programs can be associated with periodic schedules for triggering the prescribed pressure-application pattern. For example, a first program can trigger the prescribed pressure-application pattern on an hourly basis, while a second program can trigger the prescribed pressure-application pattern every 5 or 10 minutes for an hour, repeated every several hours. Other programs can trigger the prescribed pressure-application pattern on a daily basis, or on a varying schedule.

In additional implementations, the user can initiate the prescribed pattern by actuation at the wearable device 100 or via another device (e.g., smart device 160) connected with the wearable device 100. In some cases, the user can initiate the prescribed pattern via the interface 200, for example, via an interface command or button (e.g., Begin Guided Breathing). It is understood that the user can also initiate the prescribed pattern via any command interface at the wearable device 100 and/or the smart device 160, e.g., a voice interface ("Please initiate guided breathing) or a tactile interface (e.g., via double-tap), or via gesture-based commands (e.g., head nod, wrist flip). In any case, the user can actuate the prescribed pattern using one or more interface commands described herein.

In additional implementations, the controller 150 can initiate the prescribed pattern based upon a biometric indicator that indicates an elevated stress level for the user. As noted herein the biometric monitoring system 170, portions of which can be located at the wearable device 100 and/or the smart device 160, can include embedded sensors for measuring biometric information about user, e.g., travel, sleep or exercise patterns; body temperature; heart rate; or pace of gait. In some cases, the biometric monitoring system 170 includes physiological sensors for detecting biometric conditions (indicators) about the user (e.g., one or more biometric sensors such as a heart rate sensor, a photoplethysmogram (PPG), electroencephalogram (EEG), electrocardiogram (ECG)). In certain cases, these sensors can detect one or more biometric indicators that indicate an elevated level of stress in the user. For example, a heart rate sensor detecting that the user's heart rate is above a resting rate (or a resting range, specific to the user) can be used as an indicator of an elevated stress level. A similar approach can be used with heightened brain activity, as detected by an EEG. Additionally, a decrease in heart rate variability, an increase in skin conductivity and/or an increase in shallow breathing can also be used as biometric indicators that indicate an elevated level of stress in the user.

In various implementations, the controller 150 receives data (an indicator) about the biometric condition(s) from the biometric monitoring system 170. In the case that the detected biometric condition indicator deviates from a threshold, the logic in controller 150 adjusts the prescribed pattern. In some cases, the threshold is a user-specific threshold such as a heart rate range or brain activity range that defines stress level(s) for the user. In other cases, the threshold is generalized, such that an indicator (e.g., heart rate) above a particular detected level is an indicator of stress in most, if not all, individuals. It is understood that the biometric indicator thresholds can be user-defined, defined by one or more population models, and/or updated using the logic in controller 150 and/or in the smart device 160. In some cases, the logic used to detect biometric conditions (and/or other sensor processing logic) is configured to teach the logic used to define biometric indicator thresholds, e.g., where one or more of these logic components includes an artificial intelligence (AI) component for iteratively refining logic operations to enhance the accuracy of its results. Example AI components include machine learning logic, a neural network including an artificial neural network, a natural language processing engine, a deep learning engine, etc. It is further understood that the logic functions described with reference to the control system 150 and/or smart device 160, may be interconnected in such a manner that these components act in concert or in reliance upon one another.

When the controller 150 detects the biometric indicator(s) that deviates from the threshold(s), e.g., indicating an elevated level of stress, the controller 150 can adjust the prescribed pattern of pressure application. For example, the controller 150 can initiate the prescribed pattern in response to detection of the elevated level of stress (i.e., as a real-time response to stress detection). In other cases, the controller 150 can initiate the prescribed pattern at regular intervals based upon learned behavior about the user's stress levels, e.g., initiating the prescribed pattern in late-afternoon hours on weekdays to mitigate stress of the workday. In still other cases, the controller 150 can modify a current session including the prescribed pattern in response to detecting the elevated level of stress. For example, the controller 150 can decrease the frequency of repetitions, alter the pressure of one or more segments of the repetitions, etc. in order to combat detected stress in the user.

In some cases, the wearable device 100 and/or the smart device 160 can include additional sensors for gathering data in managing respiration, e.g., temperature sensors or humidity sensors for detecting changes in weather within environments, optical/laser-based sensors and/or vision systems for tracking movement or speed, light sensors for detecting time of day, additional audio sensors (e.g., microphones) for detecting human or other user speech or ambient noise, etc.

Returning to FIG. 1, in various implementations, the heat transfer member 180 is configured to heat or cool the body part of the user, before during or after one or more repetitions in the pattern. In particular cases, the controller 150 is configured to initiate a temperature change at the heat transfer member 180 in order to either heat or cool the body part of the user. For example, during one or more segments of each repetition, the controller 150 is additionally configured to initiate a temperature change at the heat transfer member 180, e.g., by increasing heating or cooling as pressure increases, and reducing heating or cooling as pressure decreases. In some cases, the controller 150 is configured to apply a change in temperature that corresponds with changes in the application of pressure from the contact element 130. This corresponding temperature change can increase the intensity of each given repetition, providing both pressure-based and temperature-based respiration triggers. In various implementations described further herein, the heat transfer member 180 can be used as an isolated mechanism for managing respiration.

Figure 3:
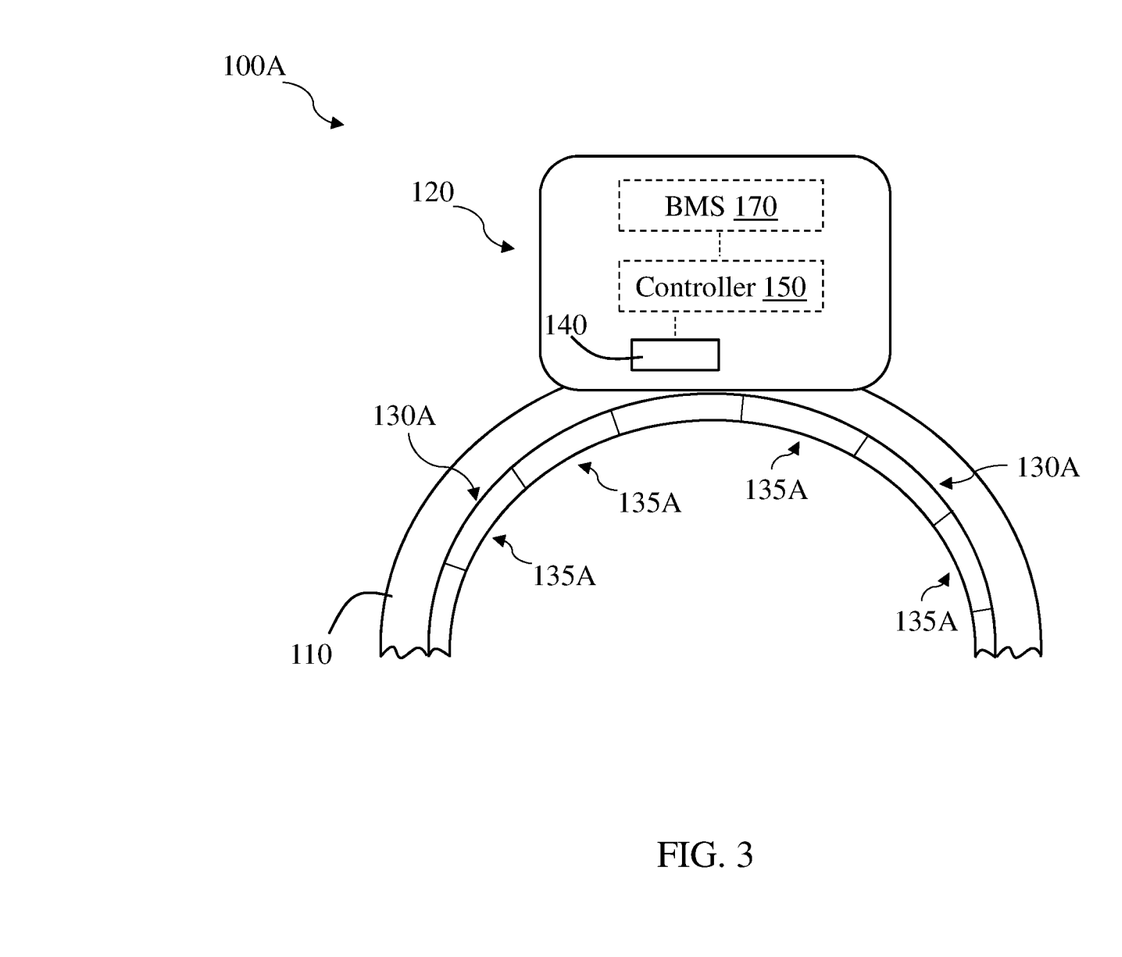
FIG. 3 is a schematic depiction of a wearable device according to various additional implementations.
Figure 4:
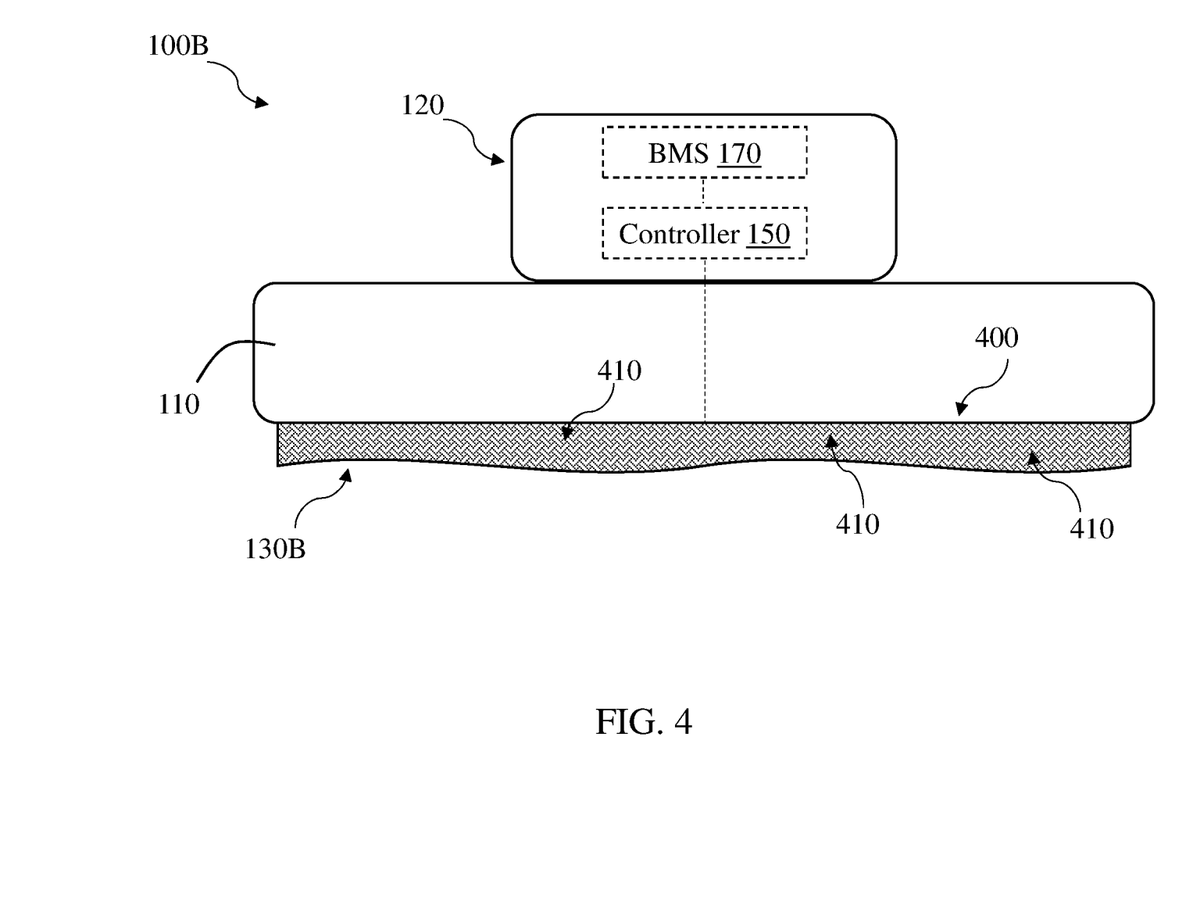
FIG. 4 is a schematic depiction of an additional wearable device according to various implementations.
Figure 5:
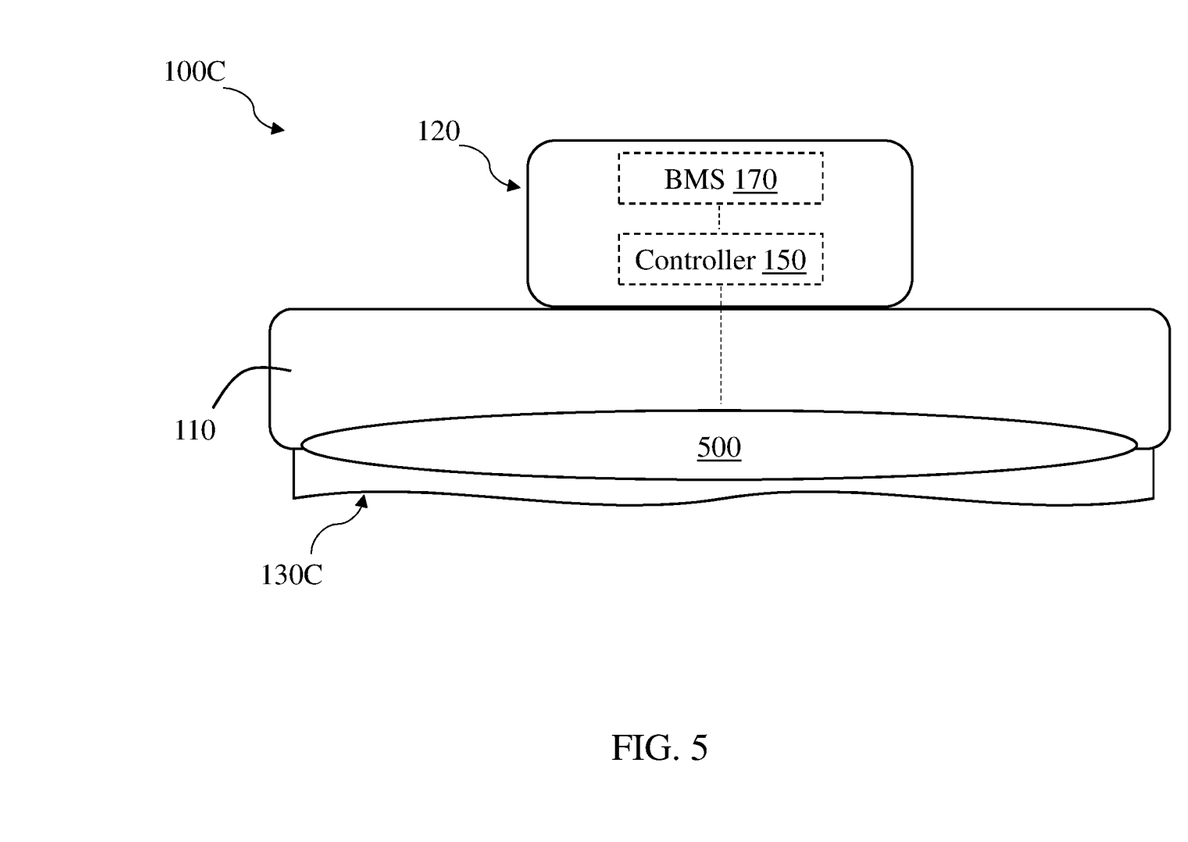
FIG. 5 is a schematic depiction of another wearable device according to various implementations.

As noted herein, the wearable device 100 can have various form factors for providing pressure-based respiration management. For example, as shown in FIG. 1, in some implementations, the wearable device 100 includes a contact element 130 that has a substantially planar contact surface 135 for applying pressure to the body part of the user (arm/wrist, leg/ankle, head, waist, etc.). FIGS. 3-5 illustrate various additional wearable devices 100A-100C according to implementations.

As shown in FIG. 3, in some cases, a wearable device 100A can include a contact element 130A having an arcuate contact surface 135A for at least partially wrapping around the body part of the user while applying pressure to that body part. In some cases, the arcuate contact surface 135A can be shaped to complement a contour on the body part, e.g., a portion of the wrist or ankle, or a portion of the ear, temple region or other portion of the head. The arcuate contact surface 135A can be substantially concave, for example, to distribute pressure across the surface of the user's body part. In certain cases, a plurality of contact elements 130A are arranged along an arc to apply pressure to distinct portions of the body part of the user. In some additional particular implementations, the plurality of contact elements 130A are positioned in an annular manner around the body part.

FIG. 4 shows an additional implementation including a wearable device 100B having a flexible contact element 130B that is actuatable using a flexible fiber 400. In these cases, the wearable device 100B can be configured to at least partially wrap around the body part of the user, e.g., to surface mount and/or to fasten around that body part. The flexible contact element 130B can include a material such as silicone, cloth and/or a synthetic that is configured to flex when the flexible fiber 400 underlying the flexible contact element 130B is actuated. In some cases, the flexible fiber 400 includes a plurality of interwoven segments 410 that are configured to expand and contract in response to actuation by the controller 150. In some particular implementations, the flexible contact element 130B wraps entirely, or nearly entirely, around the body part of the user. In these cases, the flexible fiber 400 can also extend entirely around, or nearly entirely around, the body part. In some cases, flexible fiber 400 is configured to flex (e.g., expand and contract) in order to apply pressure around that body part.

FIG. 5 shows an additional implementation including a wearable device 100C having a flexible contact element 130C that is actuatable using a bladder system. In these cases, the wearable device 100C can be configured to at least partially wrap around the body part of the user, e.g., to surface mount and/or to fasten around that body part. The flexible contact element 130C can include a material similar to the flexible contact element 130B shown in FIG. 4, e.g., silicone, cloth and/or a synthetic that is configured to flex when a bladder 500 underlying the flexible contact element 130C is actuated. In some cases, the bladder 500 is configured to fill with a fluid such as air or water, and to expand and contract in response to actuation by the controller 150. In some cases, the bladder 500 is connected with a pump and or a controllable valve for controlling the flow of fluid into and out of the bladder 500. In some particular implementations, the flexible contact element 130C wraps entirely, or nearly entirely, around the body part of the user. In these cases, the bladder 500 can also extend entirely around, or nearly entirely around, the body part. In some cases, the bladder 500 is configured to expand and contract in order to apply pressure around that body part.

Figure 6:
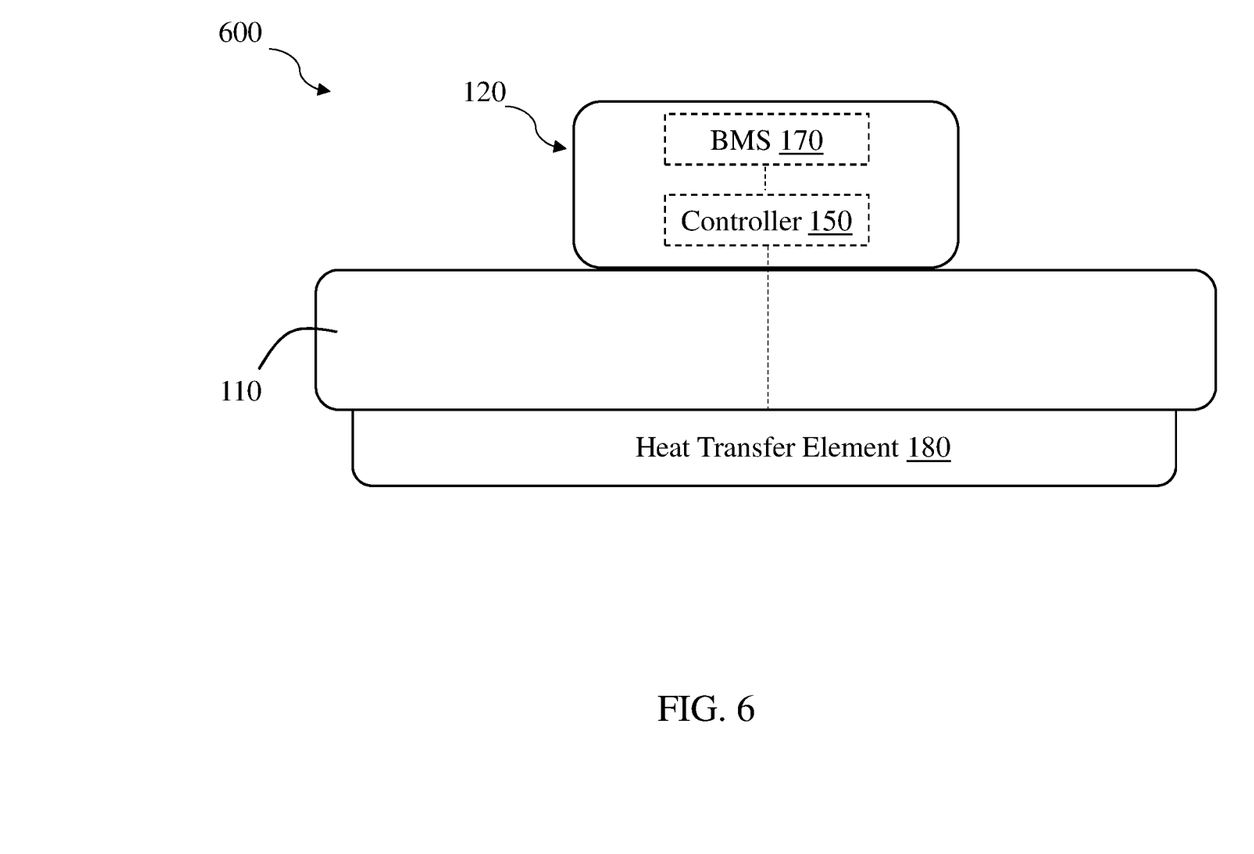
FIG. 6 is a schematic depiction of a wearable device using a heat transfer element to control respiration, according to various additional implementations.

FIG. 6 shows an additional implementation of a wearable device 600, including a heat transfer element 180 as the mechanism for managing respiration. That is, in these cases, the heat transfer element 180 can act to heat/cool the body part of the user to manage respiration, without necessarily applying pressure using a contact element (e.g., contact element 130, FIG. 1). In these cases, the wearable device 600 can include similar components as described with reference to the wearable device 100 (FIG. 1), redundant description of which is omitted. In some cases, the heat transfer element 180 can include a plurality of separate heat transfer elements, which may be individually connected with the controller 150, or at least partially serially connected with one another and the controller 150.

The controller 150 is coupled with the heat transfer element(s) 180 in order to actuate heating and/or cooling to the body part of the user according to a prescribed pattern. In various implementations, the prescribed pattern can be similar in segmentation to the prescribed pattern of pressure described herein. For example, the prescribed pattern of heating and/or cooling can include the following segments: i) a first segment at a progressively increasing or decreasing temperature; ii) a second segment at a substantially constant temperature, that follows the first segment; iii) a third segment at a progressively decreasing or increasing temperature, that follows the second segment; and iv) a fourth segment at a substantially constant temperature that is distinct from the substantially constant temperature of the second segment. In these cases, where the first segment is at a progressively increasing temperature (heating), the third segment is at a progressively decreasing temperature (cooling). In other cases, where the first segment is at a progressively decreasing temperature (cooling), the third segment is at a progressively increasing temperature (heating).

In various implementations, the controller 150 can initiate the prescribed pattern based upon a biometric indicator that indicates an elevated stress level for the user, as received from a biometric monitoring system 170 (similarly described with reference to FIG. 1). As noted herein, the biometric monitoring system 170 can include sensors configured to detect one or more biometric indicators that indicate an elevated level of stress in the user. In various implementations, the controller 150 receives data (an indicator) about the biometric condition(s) from the biometric monitoring system 170. In the case that the biometric indicator(s) deviates from the threshold(s), e.g., indicating an elevated level of stress, the controller 150 can adjust the prescribed pattern of temperature change. For example, the controller 150 can initiate the prescribed temperature application pattern in response to detection of the elevated level of stress (i.e., as a real-time response to stress detection). In other cases, the controller 150 can initiate the prescribed temperature application pattern at regular intervals based upon learned behavior about the user's stress levels. In still other cases, the controller 150 can modify a current session including the prescribed temperature application pattern in response to detecting the elevated level of stress.

While certain implementations of wearable devices are described including both contact element(s) 130 and heat transfer element(s) 180, it is understood that some implementations can rely upon only one such mechanism to manage respiration according to a prescribed pattern. In these cases, pressure or heating can act as a stand-alone respiration management mechanism, as managed by the controller 150.

Figure 7:
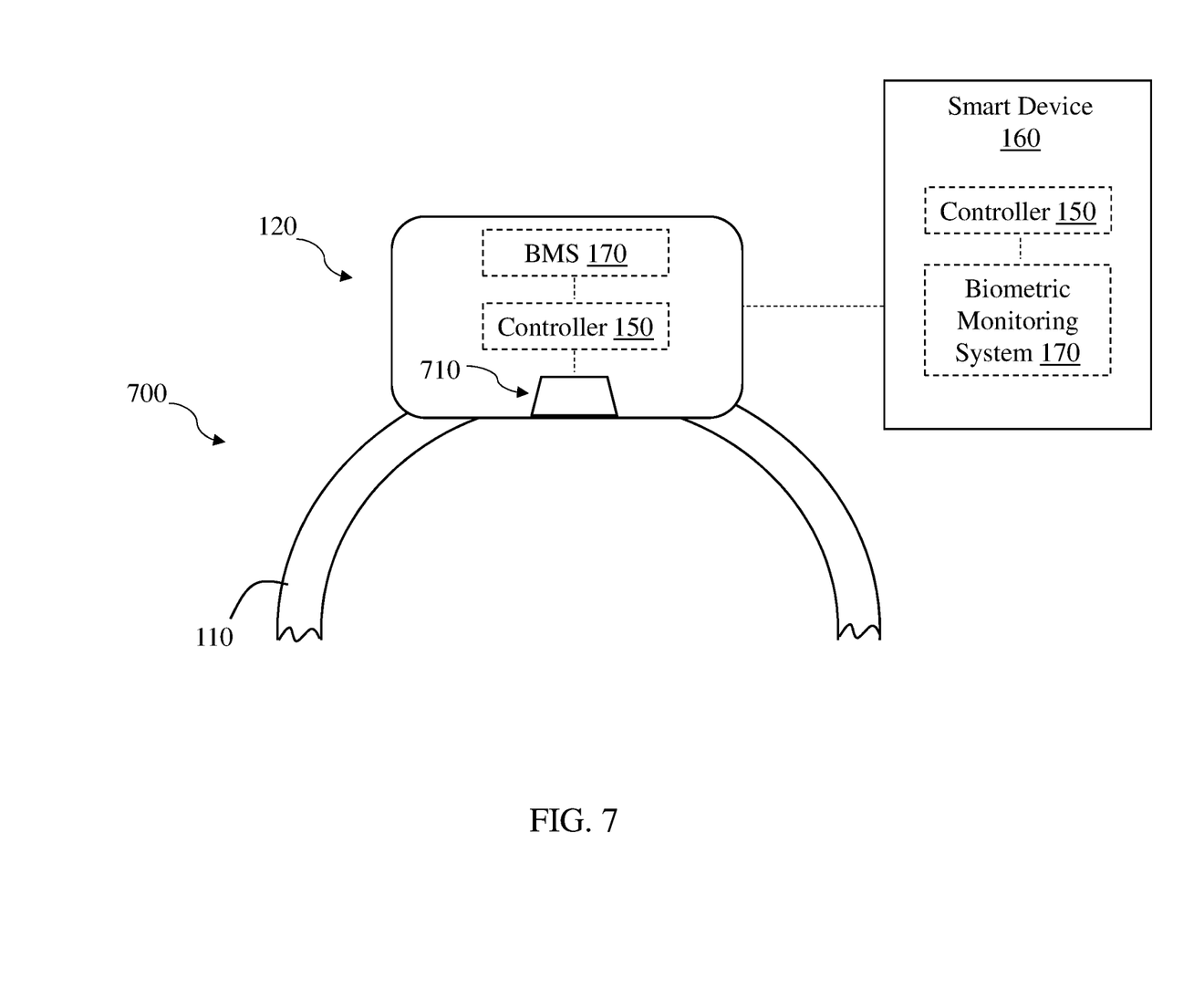
FIG. 7 is a schematic depiction of a wearable device using a transducer to control respiration, according to various additional implementations.

In still further implementations, a wearable device can be configured to manage respiration using bone conduction. This wearable device can be one of a class of advanced vibrotactile actuators that is configured to transmit soundwaves into a user's body that are audible only to the user wearing that device. FIG. 7 depicts an example wearable device 700 configured to manage respiration using bone conduction. In these implementations, the wearable device 700 can include a housing 120 similar in configuration to the housing in wearable device 100 (FIG. 1) or the other wearable devices shown and/or described herein. In these particular implementations, the wearable device 700 can include a transducer 710 coupled with the controller 150 for providing an acoustic output, i.e., transmitting soundwaves into the body part of the user. In some cases, the transducer 710 includes a low frequency speaker such as a woofer or subwoofer. In these implementation, the controller 150 can include additional control circuitry for controlling the acoustic output at the transducer 710, e.g., audio processing components such as one or more digital signal processor(s), analog to digital converter(s), etc. In various implementations, the controller 150 is configured to instruct the transducer 710 to transmit soundwaves into the body part of a user according to a prescribed pattern. In some implementations, the prescribed pattern can be similar in segmentation to the pressure-based and/or temperature-based respiration management patterns described herein. For example, the prescribed pattern of soundwave transmission can include the following segments: i) a first segment at a progressively increasing or decreasing audio modality level (e.g., frequency, tone, pitch, volume, sound pressure level (SPL) or additional musical or audio qualities); ii) a second segment at a substantially constant audio modality level, that follows the first segment; iii) a third segment at a progressively decreasing or increasing audio modality level, that follows the second segment; and iv) a fourth segment at a substantially constant audio modality level that is distinct from the substantially constant audio modality level of the second segment. In these cases, where the first segment is at a progressively increasing audio modality level, the third segment is at a progressively decreasing audio modality level. In other cases, where the first segment is at a progressively decreasing audio modality level, the third segment is at a progressively increasing audio modality level. This wearable device 700 can be configured to transmit the audio output at such a level (e.g., sound pressure level, or SPL) that only the user wearing the wearable device 700 can detect the soundwaves.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-com-

We claim:

1. A wearable device for managing respiration and health of a user, the device comprising:
   a mount sized to couple with a body part of the user, wherein the mount is sized to fit on a head region of the user; and
   a housing coupled with the mount, the housing at least partially containing:
      a contact element for applying pressure to the head region of the user, wherein the contact element comprises a plurality of contact elements arranged along an arc or configured to be positioned in an annular manner around the body part of the user; and
      an actuator coupled with the contact element, the actuator configured to actuate the contact element in applying pressure to the body part of the user according to a prescribed pattern, the prescribed pattern comprising at least two repetitions, each repetition comprising:
         a first segment at a progressively increasing pressure;
         a second segment at a substantially constant pressure, following the first segment;
         a third segment at a progressively decreasing pressure, following the second segment; and
         a fourth segment at a substantially constant pressure that is less than the substantially constant pressure of the second segment,
   wherein the wearable device comprises a head-worn wearable audio device configured to be worn on the head region of the user while not in use for managing respiration and health of the user.

2. The wearable device of claim 1, wherein the substantially constant pressure at the second segment is a maximum applied pressure for the prescribed pattern, and is applied for a period of at least approximately 0.1 second to approximately five seconds, and wherein the third segment at the progressively decreasing pressure is applied for a period of approximately four seconds to approximately 20 seconds, wherein managing respiration in the user comprises at least one of guided breathing or breathing entrainment, wherein the second segment and the fourth segment are each punctuated with an increase or decrease in pressure for less than one second to provide a signal to the user that the substantially constant pressure is over.

3. The wearable device of claim 1, wherein a later one of the repetitions immediately follows a preceding one of the repetitions,
   wherein the at least two repetitions comprises up to approximately 500 repetitions.

4. The wearable device of claim 1, wherein the housing further comprises a controller comprising a processor and logic for controlling the actuator,
   wherein the actuator comprises an electro-mechanical actuator, a pneumatic actuator or a flexible fiber actuator.

5. The wearable device of claim 4, further comprising a biometric monitoring system coupled with the controller, wherein the controller is configured to adjust the prescribed pattern according to at least one detected biometric condition indicator detected by the biometric monitoring system deviating from a corresponding threshold.

6. The wearable device of claim 4, wherein the controller is configured to receive commands from a smart device proximate the wearable device.

7. The wearable device of claim 4, wherein the controller is configured to initiate the prescribed pattern based upon a periodic schedule for the user, wherein the periodic schedule is defined by a guided breathing program or a breathing entrainment program.

8. The wearable device of claim 4, wherein the controller is configured to initiate the prescribed pattern based upon a biometric indicator indicating an elevated stress level for the user, wherein the biometric indicator is detected by a physiological sensor located at the wearable device or a smart device connected with the wearable device and configured to be worn by the user.

9. The wearable device of claim 1, further comprising a heat transfer member configured to at least one of heat or cool the body part of the user.

10. A computer-implemented method of managing respiration and health of a user with a wearable device, the method comprising:
    actuating a contact element to apply pressure to a body part of the user according to a prescribed pattern, the prescribed pattern comprising at least two repetitions, each repetition comprising:
       a first segment at a progressively increasing pressure;
       a second segment at a substantially constant pressure, following the first segment;
       a third segment at a progressively decreasing pressure, following the second segment; and
       a fourth segment at a substantially constant pressure that is less than the substantially constant pressure of the second segment,
    wherein the wearable device is a head-worn wearable audio device and is configured to be worn while not in use for managing respiration and health of the user,
    wherein the contact element comprises a plurality of contact elements arranged along an arc or configured to be positioned in an annular manner around the body part of the user.

11. The method of claim 10, wherein the substantially constant pressure at the second segment is a maximum applied pressure for the prescribed pattern, and is applied for a period of at least approximately 0.1 second to approximately five seconds, and wherein the third segment at the progressively decreasing pressure is applied for a period of approximately four seconds to approximately 20 seconds, wherein the second segment and the fourth segment are each punctuated with an increase or decrease in pressure for less than one second to provide a signal to the user that the substantially constant pressure is over.

12. The method of claim 10, wherein a later one of the repetitions immediately follows a preceding one of the repetitions.

13. The method of claim 10, further comprising:
    monitoring at least one biometric condition of the user; and
    adjusting the prescribed pattern according to the at least one biometric condition deviating from a corresponding threshold.

14. The method of claim 10, wherein the prescribed pattern is initiated based upon at least one of:
    (a) a periodic schedule for the user,
    (b) a biometric indicator indicating an elevated stress level for the user, or
    (c) actuation by the user.

15. A wearable device for managing respiration and health of a user, the device comprising:
- a mount sized to couple with a body part of the user, wherein the mount is sized to fit on a head or neck region of the user; and
- a housing coupled with the mount, the housing at least partially containing:
  - a heat transfer element configured to at least one of heat or cool the body part of the user;
  - a contact element for applying pressure to the body part of the user;
  - an actuator coupled with the contact element, the actuator configured to actuate the contact element in applying pressure to the body part of the user, wherein the actuator comprises a plurality of contact elements arranged along an arc to apply pressure to distinct portions of the body part of the user; and
  - a controller coupled with the heat transfer element and the actuator, the controller configured to actuate the heat transfer element and the actuator in the at least one of heating or cooling the body part of the user and applying pressure to the body part of the user according to a prescribed pattern, the prescribed pattern comprising at least two repetitions, each repetition comprising:
    - a first segment at a progressively increasing or decreasing temperature and a progressively increasing pressure;
    - a second segment at a substantially constant temperature and a substantially constant pressure, following the first segment;
    - a third segment at a progressively decreasing or increasing temperature and a progressively decreasing pressure, following the second segment; and
    - a fourth segment at a substantially constant temperature and pressure that is distinct from the substantially constant temperature and pressure of the second segment,
  - wherein the wearable device comprises a head-worn wearable audio device configured to be worn on a head or neck region of the user while not in use for managing respiration and health of the user.

16. The wearable device of claim 15, further comprising a biometric monitoring system coupled with the controller, wherein the controller is configured to adjust the prescribed pattern according to at least one detected biometric condition indicator detected by the biometric monitoring system deviating from a corresponding threshold.

17. The wearable device of claim 15, further comprising:
- a contact element for applying pressure to the body part of the user; and
- an actuator coupled with the contact element, the actuator configured to actuate the contact element in applying pressure to the body part of the user.

* * * * *